US00PP31809P2

(12) United States Plant Patent
Meyer

(10) Patent No.: US PP31,809 P2
(45) Date of Patent: May 26, 2020

(54) *HEMEROCALLIS* PLANT NAMED 'RASPBERRY ECLIPSE'

(50) Latin Name: ***Hemerocallis* (L.) hybrid**
Varietal Denomination: Raspberry Eclipse

(71) Applicant: Chris Meyer, Zeeland, MI (US)

(72) Inventor: Chris Meyer, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,098

(22) Filed: Aug. 6, 2019

(51) Int. Cl.
*A01H 5/02* (2018.01)

(52) U.S. Cl.
USPC ..... Plt./312

(58) Field of Classification Search
USPC ..... Plt./312
CPC ..... A01H 5/02
See application file for complete search history.

*Primary Examiner* — Annette H Para

(57) ABSTRACT

A new and distinct *Hemerocallis* plant named 'Raspberry Eclipse' characterized by winter-hardy compact habit with clean medium-green foliage possessing a purplish-bronze blush that goes dormant in the winter. The flowers are rounded, fragrant, single flowers with raspberry-purple, a lavender-purple band and are highlighted by a ruffled lemon-yellow picotee edge and light green throat. Both tepal sets are slightly reflexed with the outer tepal set having consistent, considerable, yellow crisped margins. The new plant flowers up to 67 cm tall with three-way branching beginning about mid-July.

2 Drawing Sheets

Botanical classification: *Hemerocallis* (L.) hybrid.
Variety denomination: 'Raspberry Eclipse'.

STATEMENT REGARDING PRIOR DISCLOSURES UNDER 37 CFR 1.77(B)(6)

The first disclosure, in the form of a sale, was made by Walters Gardens, Inc. on Aug. 6, 2018 to Overdevest Nurseries, L.P., Gardens Alive and Prides Corner. On Feb. 1, 2019 a photograph and brief description of the new plant were also placed on a website of Walters Gardens, Inc. and on May 29, 2019 the new plant was advertised in the Walters Gardens 19-20 Catalog. Walters Gardens, Inc. obtained the new plant and all information relating thereto, from the inventor. No plants of *Hemerocallis* 'Raspberry Eclipse' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct daylily plant, *Hemerocallis* 'Raspberry Eclipse' hereinafter also referred to as the new plant or just the cultivar name, 'Raspberry Eclipse'. *Hemerocallis* 'Raspberry Eclipse' was hybridized by the inventor, Chris Meyer, in the spring of 2004 in a greenhouse at a wholesale perennial nursery in Zeeland, Mich., USA. The new plant originated from a breeding program conducted by the inventor with the specific intention to improve the garden worthiness, expand color regimens and increase flowering period which were some of the criteria of further trials in the trial beds at the same nursery in Zeeland, Mich. The female or seed parent was 'Southern Wind' (not patented) and the male or pollen parent was 'Spiny Sea Urchin' (not patented). The new plant was selected as a single seedling from this cross, and after confidential evaluations in a trial bed beginning in 2006 in Zeeland, Mich. was assigned the breeder code 04-10-3. The new plant has been asexually propagated by division at the same wholesale nursery in Zeeland, Mich. since 2007 with all resultant asexually propagated plants having retained all the same unique traits as the original plant. *Hemerocallis* 'Raspberry Eclipse' is stable and reproduces true to type in successive generations of asexual reproduction.

There are nearly 90,000 registered daylilies with The American *Hemerocallis* Society, which is the International Cultivar Registration Authority for the genus *Hemerocallis*. In comparison to the new plant, the female parent has a pastel lavender-pink flower color with a yellow watermark, a yellow-gold braided edge and a green throat. 'Southern Wind' also has a slightly taller flower scape with more branching and more flowers. In comparison to the new plant, the male parent has a much deeper lavender flower with a gold spiny edge on the inner tepal set and a green throat. 'Spiny Sea Urchin' is also slightly taller in scape with more branches and flowers.

The most similar daylily known to the inventor are 'A Groovy Kind of Love' (not patented), 'Alpha and Omega' (not patented), 'Always Afternoon' (not patented), 'All Things to All Men' (not patented), 'Audience of One' (not patented), 'Cosmic Struggle' (not patented) and 'Repeat the Sounding Joy' (not patented).

'A Groovy Kind of Love' has flowers with pink-mauve veined petals with lavender cast, a purple rim surrounding a lavender-purple eye and green throat on slightly taller scapes. 'Alpha and Omega' has flowers with a dark pink-lavender with purple eye and lavender feathering toward a green throat, and a triple edge of grape on slightly taller scapes. 'Always Afternoon' has flowers of a medium mauve that are edged in buff, a purple eye-zone and green throat on shorter scapes. 'All Things to All Men' has flowers with a dark pink-lavender, etched in gray-lavender eye and bordered in gray-lavender with a yellow edge and green throat on slightly taller scapes with more branching and flowers. 'Audience of One' has flowers that are rose-lavender with violet-grape eye, grape-lavender and ivory edge with a yellow to green throat on slightly taller scapes. 'Cosmic Struggle' has cranberry-grape flowers etched with a dark lavender watermark and a lavender and ivory-gold edge with a green throat on similar height scapes. 'Repeat the Sounding Joy' has flowers that are pink-cranberry with cranberry etched dark lavender eye, an ivory edge and chartreuse throat on slightly taller scapes.

*Hemerocallis* 'Raspberry Eclipse' differs from all other daylilies known to the applicant, by the combination of the following traits:

1. Winter-hardy, compact habit with clean medium-green foliage with purplish-bronze blush that goes dormant in the winter;
2. Fragrant, single, limbate, rounded flowers about 15 cm across of raspberry-purple with a lavender-purple band, highlighted by a ruffled, lemon-yellow, picotee edge and light green throat;
3. Outer tepals with consistent, considerable, yellow crisped margins.
4. Tepals slightly reflexed;
5. Plants produce three-way branched scapes of about 67 cm tall with up to 14 flowers per scape;
6. Flowering begins about mid-July with excellent coverage;

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
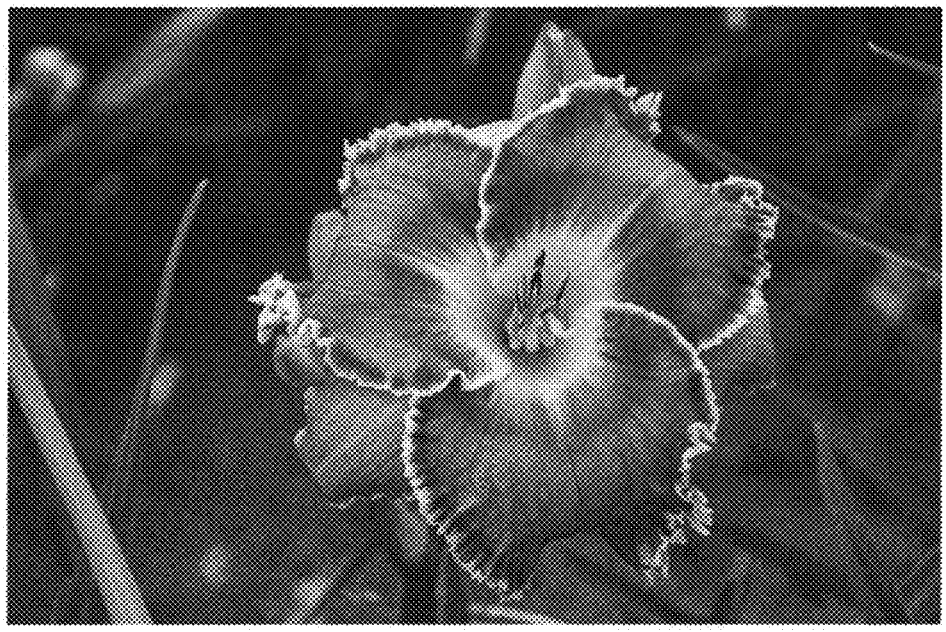
FIG. 1 shows a three-year-old plant in peak flower in a sunny landscape during mid-summer at a display garden in Zeeland, Mich.
Figure 2:
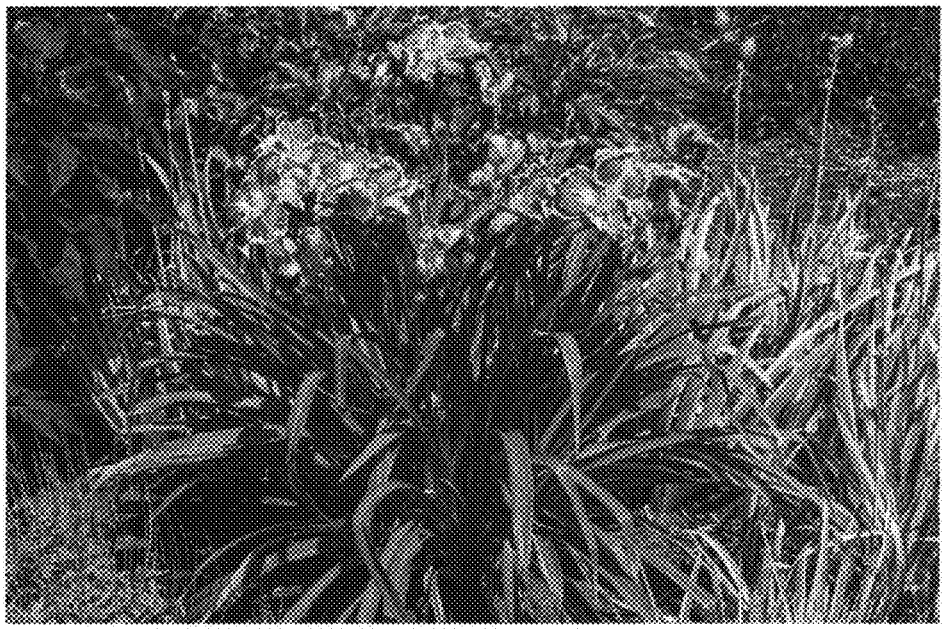
FIG. 2 shows a close-up of the flower.
Figure 3:
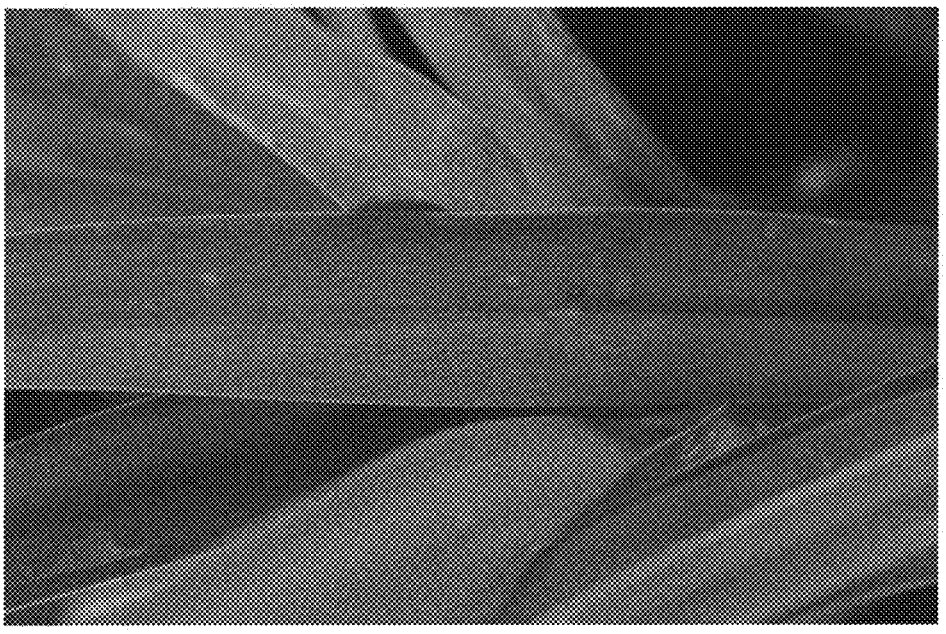
FIG. 3 shows a close-up of the foliage with purplish-bronze blush.

The following descriptions and color references are based on the 2015 edition of The Royal Horticultural Society Colour Chart except where common dictionary terms are used. The new plant, *Hemerocallis* 'Raspberry Eclipse', has not been observed under all possible environments. The phenotype may vary slightly with different environmental conditions, such as temperature, light, fertility, moisture and maturity levels, but without any change in the genotype. The following observations and size descriptions are of a three-year-old plant in a sunny landscape at a display garden in Zeeland, Michigan with and supplemental water and fertilizer.

Botanical classification: *Hemerocallis* (L.) hybrid;

Parentage: Female (seed) parent is 'Southern Wind'; male (pollen) parent is 'Spiny Sea Urchin';

Propagation: Division of the rhizome;

Growth rate: Moderate to rapid;

Crop time: About 8 to 10 weeks to flower starting in spring in a 3.8 liter container from vernalized one-year-old plant;

Rooting habit: Fleshy, about 2.5 mm diameter; lightly branching;

Root color: Nearest RHS 159C depending on soil type;

Plant shape and habit: Winter-hardy herbaceous perennial with seven basal shoots emerging from rhizomes producing a radially symmetrical mound of arching leaves;

Plant size: Foliage height about 38.0 cm tall from soil line to the top of the leaves and about 88.0 cm wide at the widest point;

Leaves: Entire, glabrous, slightly glaucous abaxial and adaxial, linear, sessile; apex narrowly acute, base sheathing; to about 67.5 cm long and 29.0 mm across, average about 61.0 cm long and about 24.0 mm across; about 15 leaves per division;

Cauline leaves: 1 to 2 per scape; reduced, average about 3.0 cm long and 9.0 mm across;

Leaf color: Young abaxial and adaxial nearest RHS 146C; mature adaxial nearest RHS 138A with blush along edges of nearest RHS 187A, mature abaxial nearest RHS 146B;

Veins: Parallel, slightly striate abaxial; color abaxial nearest RHS 137A and adaxial between RHS 137A and RHS 137B;

Flower description:

Flowers: Funnelform; single, with two sets of three tepals; 14 per scape, mostly distally arranged on typically 3 branches; upward and outwardly facing; about 15.0 cm across and 10.5 cm tall to exserted stigma, corolla about 7.5 cm deep; individually lasting for about one day; flowers remain effective from mid-July into early-August for approximately three weeks in Zeeland, Mich.;

Flower fragrance: Lightly sweet;

Buds one day prior to opening: Oblate ellipsoid with bluntly acute apex and tepals beginning to separate, and basal one-fifth narrowed terete; about 95.0 mm long and about 33.0 mm in diameter at widest point with basal one-fifth narrowing to about 12.5 mm diameter;

Buds two days prior to opening: About 75.0 mm long and 24.0 mm diameter;

Bud color one day from opening: Apical 5.0 mm nearest RHS 144A, main central portion nearest RHS 24C with faint overlay of nearest RHS 144B, narrowed base nearest RHS N144D;

Tepals: 2 sets of 3;

Inner tepals: Glabrous; rounded apex; consistently and considerably crisped margins to about 1.2 cm deep; base fused in proximal 3.0 cm; thickness at base about 3.0 mm; midrib fluted about 2.0 mm on adaxial and abaxial surface; recurved 90 degrees in distal one-fifth; about 7.5 cm across at widest point and about 13.5 cm long;

Outer tepals: Glabrous; acute apex; irregularly and slightly wavy outer margin of about 6.0 mm and central portion of ventral outer tepal mostly flat, side tepals reflexed about 90 degrees in distal on-fifth; fused in basal 3.0 cm; about 12.5 cm long and 4.5 cm across;

Inner tepal color adaxial starting distally: Outer yellow band about 10 mm wide distally and narrowing to 1.0 mm wide proximally nearest RHS 5C; inside yellow band a 3.0 mm dark purple ring nearest N77A; major outer face nearest RHS 183D with reticulate veins of nearest RHS 183B; eye about 10.0 mm wide distally nearest RHS N77C and lightening to a blend between RHS N77D and RHS 186C proximally; throat distally nearest RHS 8B and in center between RHS 1B and RHS 150B with a midrib of nearest RHS 11C;

Inner tepal color abaxial: Outer yellow band about 10 mm wide distally and narrowing to 1.0 mm wide proximally nearest RHS 5C; inside yellow band major inner face nearest between RHS 182C and RHS 1 86C; central 15 mm longitudinal stripe between RHS 29C and RHS 29D; basal 15 mm between RHS 150C and RHS 150D;

Outer tepal color adaxial: Distal half nearest RHS 183D; center nearest RHS 10B transitioning to between RHS 154B and RHS 145A in throat;

Outer tepal color abaxial: 1.0 mm green apex nearest RHS 143A; distal longitudinal center nearest RHS 22C, distal edges nearest RHS 182D; basal 3.5 cm nearest RHS 145C;

Pedicel: Approximately 12.0 mm long, 6.0 mm wide at base;

Pedicel color: Nearest RHS 144A;

Peduncle: Usually one per division, erect to about 62.0 cm tall and 9.0 mm diameter at base, average 55.0 cm tall; extending above foliage;

Peduncle color: Nearest RHS 138A;

Gynoecium: Single; tri-carpelled;

*Style*.—Single, about 10.0 cm long, 2.0 mm diameter, curled upward at distal one-third; color distally nearest RHS 4A and proximally nearest RHS 23D.

*Stigma*.—1.0 mm to 2.0 mm in diameter; color lighter than RHS 160D.

*Ovary*.—Ellipsoidal, about 8.0 mm long and 4.0 mm diameter at base with an acute apex; color nearest RHS 145A.

Androecium: Six;

*Filaments*.—Six; adnate to inner tepal in basal 2.5 cm; curving slightly upward the last 3.0 cm; about 5.2 cm long from fusion point on tepal and basally applanate, 4.0 mm across and 2.0 mm thick; color distally nearest RHS 183B and proximally nearest RHS 4A.

*Anthers*.—Oblong; dorsifixed, longitudinal; about 10.0 mm long and 2.5 mm wide; color closest to RHS 200A.

*Pollen*.—Elliptical, less than 0.1mm long; color nearest RHS 17A.

Fruit: Oblong ellipse; non-fleshy, dehiscent, many-seeded, tri-loculicidal capsule; ellipse; about 2.5 cm long and 1.5 cm in diameter; color while maturing nearest RHS 146C and at dehiscence nearest RHS 161B;

Seed: About 3 to 10 per capsule; nearly-round dried berry; about 4.0 mm diameter; color nearest RHS 202A;

Disease and pest resistance and tolerance: 'Raspberry Eclipse' has not shown resistance to diseases and pests beyond that common for daylilies, and given the northern testing regions the new plant has not been exposed to daylily rust, *Puccinia hemerocallidis*. The plant grows best and shows best coloration with plenty of moisture, adequate drainage and light shade during the hottest period of the day, but is able to tolerate some drought when mature and direct sun without leaf burn when provided sufficient water.

Hardiness at least from USDA zone 3 through 9, and other disease resistance and tolerance is typical of that of other daylilies. The new plant is useful for landscaping en masse, as a single specimen or small groups.

The invention claimed is:

1. A new and distinct ornamental daylily plant cultivar named *Hemerocallis* 'Raspberry Eclipse' as herein described and illustrated.

* * * * *